(12) United States Patent
Hodges

(10) Patent No.: US 8,198,290 B2
(45) Date of Patent: Jun. 12, 2012

(54) METHOXATIN DERIVATIVES

(75) Inventor: John C. Hodges, Ann Arbor, MI (US)

(73) Assignee: Berry and Associates, Inc., Dexter, MI (US)

( * ) Notice: Subject to any disclaimer, the term of this patent is extended or adjusted under 35 U.S.C. 154(b) by 355 days.

(21) Appl. No.: 12/646,234

(22) Filed: Dec. 23, 2009

(65) Prior Publication Data

US 2011/0152526 A1 Jun. 23, 2011

(51) Int. Cl.
*C07D 491/20* (2006.01)
*C07D 471/04* (2006.01)
*A61K 31/4747* (2006.01)
*A61K 31/4745* (2006.01)

(52) U.S. Cl. ............. 514/278; 514/292; 546/15; 546/84
(58) Field of Classification Search ................... 514/292, 514/278; 546/15, 84
See application file for complete search history.

(56) References Cited

U.S. PATENT DOCUMENTS

| 2003/0148169 | A1 | 8/2003 | Willner et al. |
| 2004/0245101 | A1 | 12/2004 | Willner et al. |
| 2005/0130248 | A1 | 6/2005 | Willner et al. |
| 2006/0199187 | A1* | 9/2006 | Meyerhoff et al. ............... 435/6 |
| 2006/0199241 | A1 | 9/2006 | Yim et al. |
| 2006/0269826 | A1 | 11/2006 | Katz et al. |
| 2008/0051428 | A1 | 2/2008 | Davis et al. |

FOREIGN PATENT DOCUMENTS

| JP | 63301883 | 8/1988 |
| JP | 63216883 | 9/1988 |

OTHER PUBLICATIONS

Ameyama, M.; Nonobe, M.; Shinagawa, E.; Matsushita, K.; Adachi, O.; *Anal. Biochem.*, 151, 263-7 (1985).
Hauge, J.G.; *J. Biol. Chem.*, 239, 3630-9 (1964).
Anthony, C.; Zatman, L.J.; Biochem. J., 104, 960-9 (1967).
Salisbury, S.A.; Forrest, H.S.; Cruse, W.B.; Kennard, O.; *Nature*, 280, 843-4 (1979).
Westerling. J.; Frank, J.; Duine, J.A.; *Biochem Biophys Res Commun*, 87, 719-24 (1979).
Killgore, J.; Smidt, C.; Duich, L.; Romero-Chapman, N.; Tinker, D.; Reiser, K.; Melko, M.; Hyde, D.; Rucker, R.B.; *Science*, 245, 850-2 (1989).
Kasahara, T.; Kato, T.; *Nature*, 422, 832 (2003).
Choi, O.; Kim, J.; Kim, J.-G.; Jeong, Y.; Moon, J. S.; Park, C. S.; Hwang, I.; *Plant Physiology* 146: 657-668 (2008).
Martin, P.; Steiner, E.; Auer, K.; Winkler, T.; *Helv. Chim. Acta*, 76, 1667-73 (1993).
Hendrickson, J.B.; deVries, J.G.; *J. Org. Chem.*, 50, 1688-95 (1985).
Corey, E.J.; Tramontano, A.; *J. Am. Chem. Soc.*, 103, 5599-5600 (1981).
Itoh, S.; Ohshiro, Y.; *Natural Product Rep.*, 45-53 (1995).
Zayats, M.; Willner, B.; Willner, I.; *Electroanalysis*, 20, 583-601 (2008).

Misset-Smits, M.; Oltshoorn, A.J.J.; Dewante, A.; Duine, J.A.; *Methods in Enzymol.*, 280, 89-98 (1997).
Itoh, S., Inoue, T., et al., "Regioselective Transformation of the Functional Groups of Coenzyme PQQ", The Chemical Society of Japan, Chemistry Letters, 1990, pp. 1675-1678.
Itoh, S., Nii, K., et al., "Novel Addition of Nitroalkanes to o-Quinones", Tetrahedron Letters, vol. 28, No. 34, 1987, pp. 3975-3978.
Itoh, S., Ogino, M., et al., "C-4 and C-5 Adducts of Cofactor PQQ (Pyrroloquionolinequinone). Model Studies Directed toward the Action of Quinoprotein Methanol Dehydrogenase", J. Am. Chem. Soc., vol. 115, No. 22, 1993, pp. 9960-9967.
Mure, M., Nii, K., et al., "The Reaction of Coenzyme PQQ with Hydrazines", J. Chem. Soc. Perkin Trans., vol. 2, 1990, pp. 315-320.
Zayats, M., Katz, E., and Willner, I., "Electrical Contacting of Flavoenzymes and NAD(P)$^+$-Dependent Enzymes by Reconstitution and Affinity Interactions on Phenylboronic Acid Monolayers Associated with Au-Electrodes", J. Am. Chem. Soc., vol. 124, 2002, pp. 14724-14735.
Zayats, M., Katz, E. and Willner, I., "Electrical Contacting of Glucose Oxidase by Surface-Reconstitution of the Apo-Protein on a Relay-Boronic Acid-FAD Cofactor Monolayer", J. Am. Chem. Soc., vol. 24, No. 10, 2002, pp. 2120-2121.

* cited by examiner

*Primary Examiner* — Joseph Kosack
*Assistant Examiner* — Matthew Coughlin
(74) *Attorney, Agent, or Firm* — Brinks Hofer Gilson & Lione

(57) ABSTRACT

The present invention provides for compounds of Formula I and II:

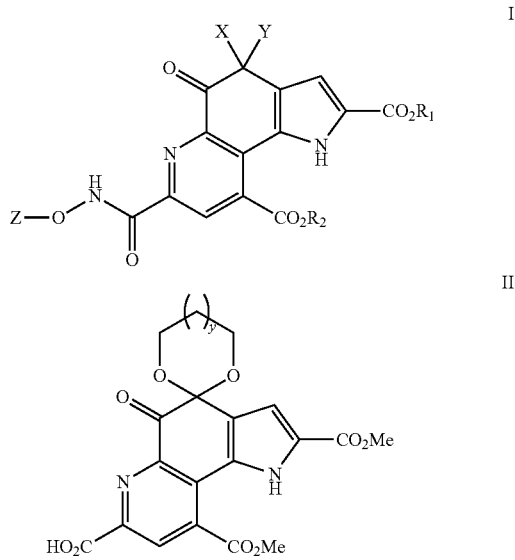

wherein y, X, Y, Z, $R^1$, and $R^2$ have any of the values defined there for in the specification. The compounds of formula I are useful as reagents in the isolation and the assay of PQQ dependent enzymes. Also provided are compositions comprising compounds of Formula I and II.

20 Claims, No Drawings

METHOXATIN DERIVATIVES

BACKGROUND

Methoxatin (pyrroloquinoline quinone or PQQ) is a coenzyme for various oxidoreductases, including alcohol dehydrogenase, aldehyde dehydrogenase and D-glucose dehydrogenase. (Ameyama et al., *Anal. Biochem.*, 151, 263-7 (1985)). Methoxatin was originally discovered in bacteria (Hauge, *J. Biol. Chem.*, 239, 3630-9 (1964); Anthony et al., *Biochem. J.*, 104, 960-9 (1967); Salisbury et al., *Nature*, 280, 843-4 (1979); and Westerling et al., *Biochem Biophys Res Commun*, 87, 719-24 (1979)). Methoxatin was later determined to have a nutritional role in mammals (Killgore et al., *Science*, 245, 850-2 (1989); and Kasahara et al., *Nature*, 422, 832 (2003)) and to exhibit a growth role in plants. (Choi et al., *Plant Physiology* 146: 657-668 (2008)). Those proteins that bind methoxatin as a coenzyme are also known as quinoproteins.

The widespread occurrence of methoxatin in nature led to exploration of its chemistry. Methods for synthesizing methoxatin have been published (see e.g., Martin et al., *Helv. Chim. Acta*, 76, 1667-73 (1993); Hendrickson et al., *J. Org. Chem.*, 50, 1688-95 (1985); Corey et al., *J. Am. Chem. Soc.*, 103, 5599-5600 (1981); and Itoh et al., *Natural Product Rep.*, 45-53 (1995)). The synthesis of solid-supported derivatives of methoxatin has been reported. (Zayats et al., *Electroanalysis*, 20, 583-601 (2008); US2003/0148169; US2004/0245101; US2005/0130248; and US2006/0269826). PQQ co-factor-macromolecule conjugates that have been used in enzyme-amplified detection and diagnostic applications (US2006/0199187 and US2006/0199241).

There is a need in the art for additional methoxatin derivatives which can be used in diagnostic and biological applications.

BRIEF SUMMARY

The present invention provides for compounds of Formula I, or a salt thereof:

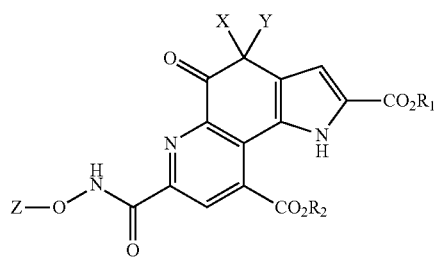

Wherein $R^1$ and $R^2$ are independently selected from the group consisting of H, $CH_3$, $C_2H_5$, $-CH_2Ph$, Ph, t-Bu, $-CH_2CH_2Si(CH_3)_3$, $-CH_2CCl_3$, $-CH_2-CHCH_2$, and $-CH_2CH_2CN$;

X and Y are the same and are selected from the group consisting of:
$-OH$, $-OCH_3$, $-OC_2H_5$, or $-OCH_2Ph$, or X and Y are taken together to form a cyclic group of $-OCH_2CH_2O-$ or $-OCH_2CH_2CH_2O-$, or X and Y are taken together to form an oxo group ($=O$);

Z is H, $R^3$-T- or $R^4-S-S-T-$:

T is selected from the group consisting of: $-(CH_2)_n-$, $-(CH_2)_n-(OCH_2CH_2)_m-$, $-(CH_2)_n-(OCH_2CH_2CH_2)_m-$, $-(CH_2)_n-$, $-CH_2C(=O)NHO-(CH_2)_n-(OCH_2CH_2)_m-$, $-CH_2C(=O)NHO-(CH_2)_n-$, $-CH_2C(=O)NHO-(CH_2)_n-(OCH_2CH_2CH_2)_m-$, $-(CH_2C(=O)NH)-$, $-(CH_2)_n-$, $-(CH_2CH_2C(=O)NH)_m-(CH_2)_n-$, $-(CH_2)_n-(NHC(=O)CH_2)_m-$, $-(CH_2)_n-(OCH_2CH_2)_m-CH_2NHC(O)-$, and $-(NHC(=O)CH_2CH_2)_m-$, wherein n is an integer from 2 to 12, m is an integer from 1 to 6;

$R^3$ is selected from the group consisting of: $H_2C=CH-$,

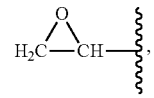

$H_2C=CHCH_2O-$,

$HOCH_2CH(OH)-$, $HOCH_2CH(OH)CH_2O-$, $HC≡C-$, $HC≡CCH_2O-$, $(Ph)_3CS-$, $HS-$, $Tr-S-$, $(HO)_2B-$, $(PhO)_2B-$, $(CH_3O)_2B-$, $CF_3(CF_2)_f(CH_2)_g-$, and $-N_3$, wherein f is an integer from 1 to 11, g is 0 or an is an integer from 1 to 3; and $R^4$ is selected from the group consisting of: $CF_3(CF_2)_f(CH_2)_g-$, pyridine-2-yl, 5-nitropyridin-2-yl, $N_3-T-$, $HC≡C-T$, $HC≡CCH_2O-T$, $(HO)_2B-T-$, and

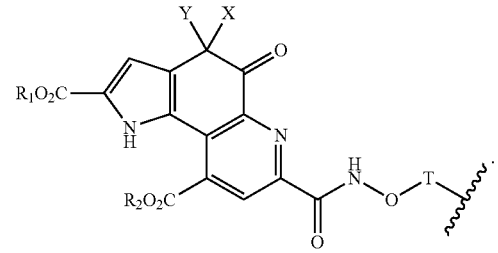

In particular embodiments, $R^1$ and $R^2$ are both H. In other embodiments, X and Y are taken together to form an oxo group. In yet other embodiments, X and Y are taken together to form a cyclic group of $-OCH_2CH_2O-$ or $-OCH_2CH_2CH_2O-$. In certain embodiments, Z is $R^3$-T-. In other embodiments, Z is $R^4-S-S-T-$.

In another aspect, the present invention provides for compounds of formula II, or a base addition salt thereof:

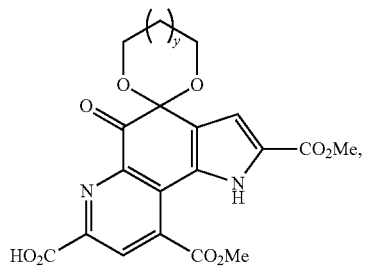

wherein y is 0 or 1. In certain embodiments, the compound is

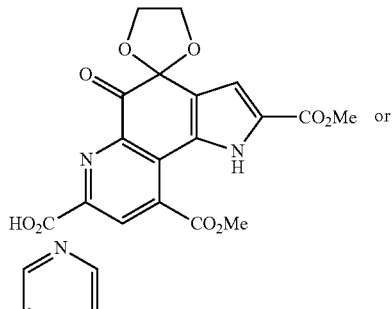

In another aspect, the present invention provides for methods of synthesizing a compound of formula II, or a pyridine salt thereof:

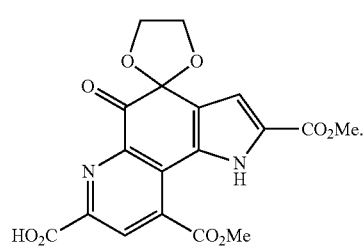

comprising contacting a compound of formula

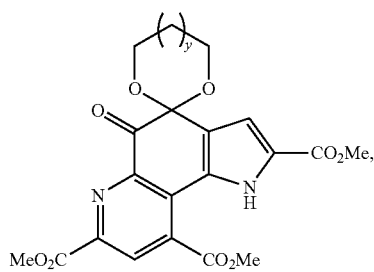

wherein y is 0 or 1, with a mixture of about 1 to about 5 parts pyridine to one part water for at least about 2 days at 20 to 30° C. In certain embodiments, the compound is

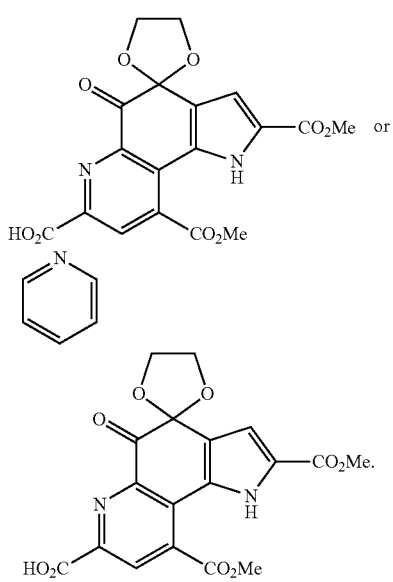

DEFINITIONS

"DCC" means N,N'-dicyclohexylcarbodiimide.
"DCM" means dichloromethane.
"DIC" means N,N'-diisopropylcarbodiimide
"DMT" means bis(4-methoxyphenyl)(phenyl)methyl, also known as dimethoxytrityl.
"DNA" means (2'-deoxyribo)nucleic acid.
"EDAC.HCl" means 1-ethyl-3-(3-dimethylaminopropyl) carbodiimide hydrochloride.
"EtOAc" means ethyl acetate.
"GDH" means glucose dehydrogenase.
"Heteroatom" means a nitrogen atom, an oxygen atom, or a sulfur atom.
"HOAT" means 1-hydroxy-7-aza-benzotriazole.
"HOBT" means 1-hydroxy-benzotriazole.
"i-Pr" means isopropyl, 2-propyl, or —CH(CH$_3$)$_2$.
"Me" means methyl or CH$_3$.
"MeCN" means acetonitrile.
"MeOH" means methanol.
"Mono-salt" means only one salt within a single compound. For example with a tricarboxylic acid compound, the addition of one molar equivalent of a base creates a mono-salt.
"Ph" means phenyl or C$_6$H$_5$.
"Poly-salt" means more than one salt within a single compound. For example with a tricarboxylic acid compound, the addition of either two or three molar equivalents of a base creates a poly-salt. Examples of poly-salts include di-salts and tri-salts.
"PYBOP" means (benzotriazo-1-yloxy)tripyrrolidino-phosphonium hexafluorophosphate.
"Quinoprotein" means a protein or enzyme that utilizes the quinone cofactor, methoxatin.
"Regiochemistry" means the single or multiple positions of a molecule where a chemical reaction takes place.
"Regioselective" means one position of a molecule is preferred among two or more possible positions. A regioselective reaction is one in which one direction of bond making or breaking occurs preferentially over all other possible directions. Reactions are termed completely regioselective if the discrimination is complete (100%), or partially regioselective, if the product of reaction at one site predominates over the product of reaction at other sites (i.e. >50% if there are two sites).

"Regiospecific" means 100% regioselective.
"RNA" means ribonucleic acid.
"t-Bu" means tertiary-butyl or $C(CH_3)_3$.
"THF" means tetrahydrofuran.
"TLC" means thin layer chromatography.
"Tr" means triphenylmethyl, also known as trityl.

DETAILED DESCRIPTION

The structure of methoxatin with ring numbering may be depicted as the following formula:

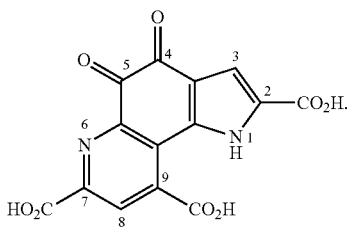

The present invention relates to hydroxamic acid derivatives at the 7-position of methoxatin. The preparation and use of these compounds is described in more detail below and in the examples.

Scheme 1

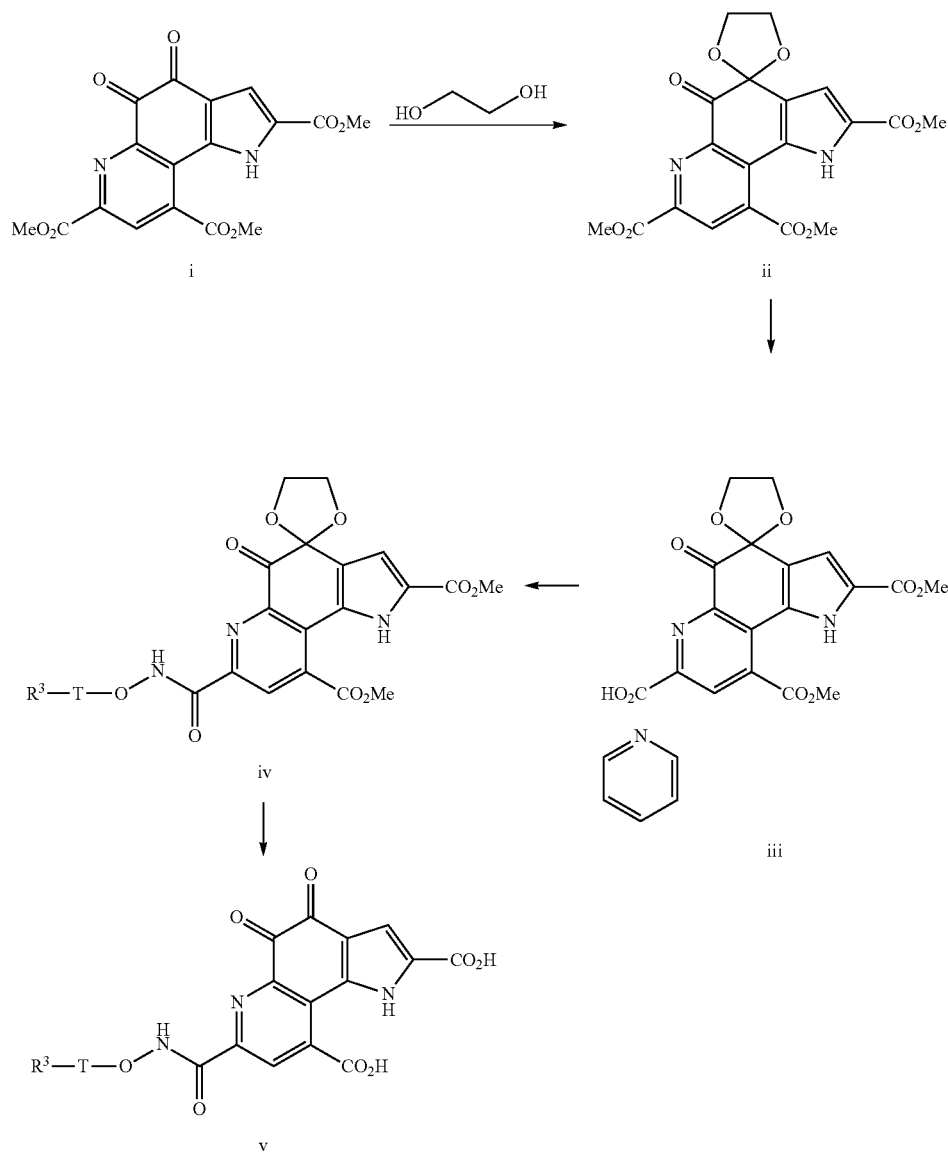

A general synthetic route for preparing compounds of formula I is set forth above in Scheme 1. The quinone functionality of methoxatin trimethyl ester (i) (which may be prepared according to Martin et al., *Helv. Chim. Acta,* 76, 1667-73 (1993)) may be protected by reaction with ethylene glycol (or similarly with propane-1,3-diol) and a catalytic amount of an acid such as p-toluenesulfonic acid, benzenesulfonic acid, or camphorsulfonic acid in refluxing benzene or toluene, utilizing a Dean-Stark trap to remove water produced by the reaction. The resulting ketal-protected compound (II) may then be dissolved in pyridine-water and allowed to stir at about room temperature for several days (e.g., 4-10 days). These very mild conditions result in saponification of the methyl ester at the 7-position with extraordinarily high regioselectivity. Coupling of (iii) with O-substituted-hydroxylamines (i.e., $R^3$-T-O—$NH_2$) using reagents such as EDAC.HCl, DCC or DIC in combination with HOBT or HOAT, or PYBOP in combination with a tertiary amine base such as triethylamine or diisopropylethylamine affords compound (iv). After purification of (iv) by chromatography only a single regioisomer is typically observed by $^1$H-NMR. The ketal protecting group may then be removed by acid hydrolysis (e.g., dilute HCl) to liberate the quinone functionality. Saponification of the remaining two methyl esters may then be accomplished by treatment with a hydroxide base, such as, for example, LiOH, NaOH, or KOH, to provide (v). The synthesis outlined in Scheme 1 provides a generally applicable strategy for the regiospecific introduction of hydroxamic acid modifications to methoxatin at the 7-position, leaving the 2 and 9 positions of methoxatin as free carboxylic acids or their base addition salts.

In certain embodiments, the compounds of the present invention, e.g., compounds of formulas I and II may be capable of forming salts. Acceptable base addition salts may be formed with metals or amines, such as alkali and alkaline earth metal hydroxides, or of organic amines Examples of metals used as cations are aluminum, calcium, magnesium, potassium, sodium, lithium, and the like. Examples of suitable amines include tertiary amines, such as triethylamine, N,N-di(isopropyl)-ethylamine, N-methylmorpholine, N-methylpiperidine, N-methylpyrrolidine, and the like, and aromatic amines, such as pyridine, 2,6-dimethylpyridine, 2,4,6-trimethylpyridine, 4-(dimethylamino)pyridine, and the like.

In a particular embodiment, a compound of formula II may form a pyridine salt.

In certain embodiments, the compounds of formula I retain the natural co-enzyme activity of methoxatin, indicating that the compound is still recognized as methoxatin by the enzymes for which it is a co-factor. In certain embodiments, the compounds of formula I retain from 1% to 100 of the activity of native methoxatin using the GDH assay of Example 14. In certain embodiments, the compounds of formula I retain greater than 5% activity of native methoxatin, 10% activity of native methoxatin, greater than 15% activity of native methoxatin, greater than 20% activity of native methoxatin, greater than 25% activity of native methoxatin, greater than 30% activity of native methoxatin, greater than 35% activity of native methoxatin, or greater than 40% activity of native methoxatin using the GDH assay of Example 14. In certain embodiments, the compound of formula I retain between about 40% to about 100% of the activity of native methoxatin using the GDH assay of Example 14.

Compounds of formula I may be used to prepare antibodies against PQQ which can be used to isolate and or assay for quinoproteins. For example, a compound of formula I may be reacted with an antigenic carrier protein (e.g., keyhole limpet hemocyanin (KLH), serum albumin, bovine thyroglobulin, or soybean trypsin inhibitor). In certain embodiments, the compound of formula I that may be employed is a compound of formula I with a free thiol group, which may react with a free thiol group on the carrier protein to form a disulfide bond. The resulting compound-carrier protein conjugate may then be used to induce polyclonal antibodies against the compound of formula I in an animal. The immunization of the animals can be by any method known in the art. See, e.g., Harlow and Lane, *Antibodies: A Laboratory Manual*, New York: Cold Spring Harbor Press, 1990. Methods for immunizing non-human animals such as mice, rabbits, rats, sheep, goats, pigs, cattle and horses are well known in the art. See, e.g., Harlow and Lane, supra. Subsequently, antibodies to methoxatin may be isolated from the mammal's blood.

Methoxatin antibodies would be useful in biochemical assays that employ methoxatin as an enzyme cofactor. For example, the methoxatin antibodies could be immobilized on a solid support and used to scavenge methoxatin from an assay solution. In certain embodiments, the compound of formula I that may be employed is a compound of formula I with a terminal —$N_3$ group as $R^3$ or $R^4$. Compounds of formula I may also be used to purify methoxatin antibodies and quinoproteins (e.g., GDH from a biological source such as *Aspergillus niger* or *Acinetobactercalcoaceticus*). A wide variety of chemistries may be employed to couple compounds of formula I to solid supports and chromatographic media that can be employed in affinity purification methods to isolate, identify, or assay quinoproteins. For example, a compound of formula I may be reacted with solid cross-linked dextran gel particles. or agarose particles. The resulting (formula I)-dextran gel or (formula I)-agarose materials may then be used in column chromatography to identify and purify quinoproteins, such as glucose dehydrogenase. The purified glucose dehydrogenase can be used to assay for glucose, which has applications in the diagnosis and treatment of diseases such as diabetes. For example, an affinity column may be prepared using a compound of formula I. For example, an azide-containing compound of formula I may be reacted with phosphine-modified solid agarose beads. The resulting agarose-compound conjugate may then be used to purify a quinoprotein or methoxatin antibody.

In addition, an affinity purification of methoxatin antibodies or a quinoprotein may be carried out by incubating a compound of formula I containing a $CF_3(CF_2)_f(CH_2)_g$— group at $R^3$, where f is an integer from 1 to 11, g is 0 or an is an integer from 1 to 3 (e.g., a $CF_3(CH_2)_7$— group) with an impure source of methoxatin antibodies or quinoprotein. The resulting mixture may be then adsorbed onto silica gel containing fluorohydrocarbon side chains (e.g., $CF_3(CH_2)_7$—) (e.g., fluorous SPE (F-SPE) cartridge ("Fluorous Solid-Phase Extraction), Fluorous Technologies, Inc., Pittsburgh, Pa.) and rinsed with water. The methoxatin antibodies or quinoprotein may then be eluted with a solution of methoxatin (alternatively a compound of formula I could be used) to elute purified methoxatin antibodies or quinoprotein.

EXAMPLES

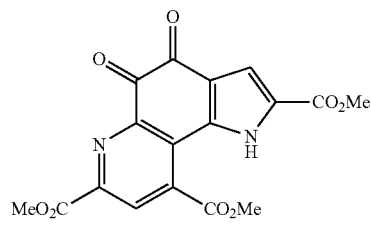

1

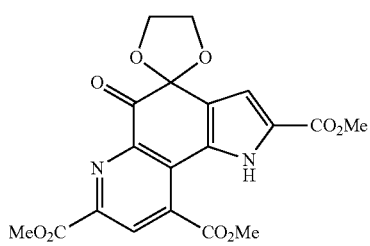

2

Example 1

Trimethyl 5'-oxo-1',5'-dihydrospiro[[1,3]dioxolane-2,4'-pyrrolo[2,3-f]quinoline]-2',7',9'-tricarboxylate (2)

A suspension of trimethyl 4,5-dioxo-4,5-dihydro-1H-pyrrolo[2,3-f]quinoline-2,7,9-tricarboxylate, 1 (1.2 g, 3.22 mMol) in benzene (200 mL) was treated with ethylene glycol (10 mL) and p-toluenesulfonic acid (60 mg, 0.32 mMol). The resulting mixture was heated at reflux under a Dean-Stark trap and reflux condenser for 14 hours. The orange suspension became a yellow solution. The heat was turned off, the trap was removed, and the condenser was replaced. To the hot solution, a mixture of benzene (75 mL) and DCM (75 mL) was cautiously added. The resulting solution was allowed to cool to room temperature, and then washed with 5% aqueous NaHCO₃ (100 mL). The organic layer was separated and washed with water (100 mL). The organic layer was separated, dried over Na₂SO₄, and filtered. Evaporation of solvent at reduced pressure gave a yellow solid. Flash chromatography on silica gel (40 g), eluting with EtOAc-DCM-Hexane (50:25:25) gave purified 2 (1/02 g, 74.4%) as a yellow solid upon evaporation of solvent. ¹H-NMR (CDCl₃, δ) 12.31 (s, 1H, NH), 8.77 (s, 1H, H-8), 7.15 (d, 1H, H-3), 4.35 (m, 2H, OCH₂), 4.30 (m, 2H, OCH₂), 4.11 (s, 1H, CO₂CH₃), 4.07 (s, 1H, CO₂CH₃), 3.93 (s, 1H, CO₂CH₃).

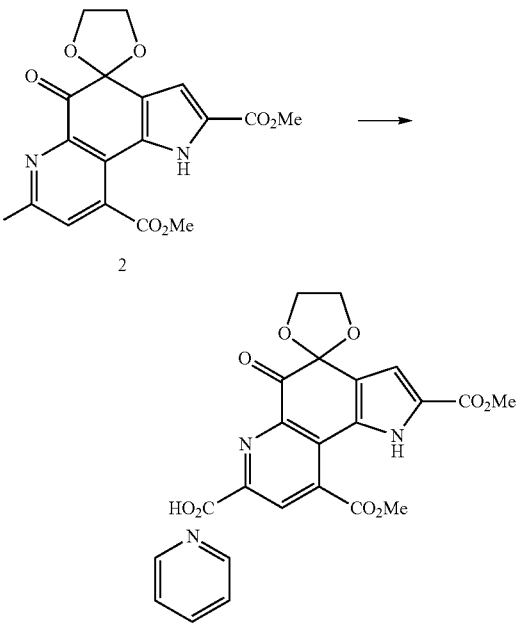

Example 2

2',9'-Bis(methoxycarbonyl)-5'-oxo-1',5'-dihydrospiro[[1,3]dioxolane-2,4'-pyrrolo[2,3-f]quinoline]-7'-carboxylic acid, pyridine salt (3)

A solution of the product from EXAMPLE 1 (2, 1.0 g, 2.4 mMol) in a mixture of pyridine (75 mL) and water (25 mL) was stirred in a capped flask at room temperature for 5 days. The reaction mixture was concentrated at reduced pressure to give an oil that begins to crystallize. Trituration with EtOAc (40 mL) gave a slurry of yellow solid, which was collected by filtration. After drying to constant weight, 3 (0.91 g, 78.8%) was isolated. NMR (DMSO-d₆, δ), 13.82 (Br, 1H, NH), 8.68 (d, 2H, 2,6-pyridine-H), 8.58 (s, 1H, H-8), 8.02 (m, 1H, 4-pyridine-H), 7.58 (m, 2H, 3,5-pyridine-H) 7.01 (d, 1H, H-3), 4.25 (m, 2H, OCH₂), 4.14 (m, 2H, OCH₂), 3.93 (s, 3H, CO₂CH₃), 3.83 (s, 3H, CO₂CH₃).

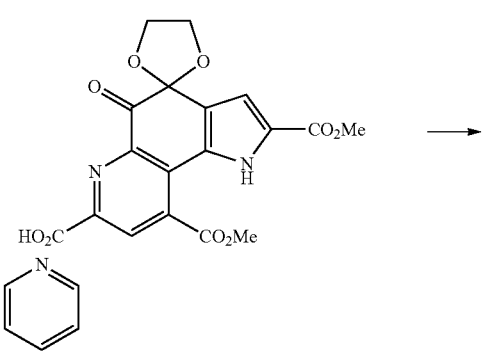

3

-continued

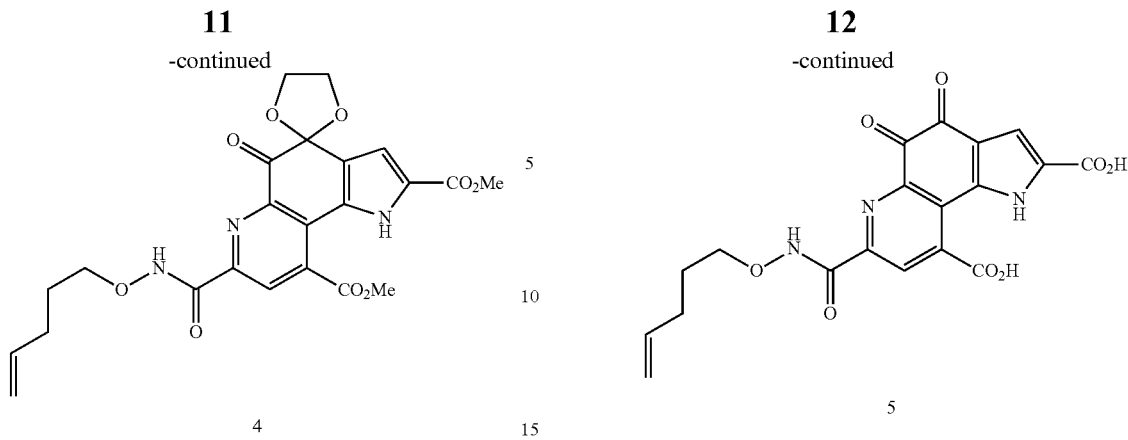

4

Example 3

Dimethyl 5'-oxo-7'-((pent-4-en-1-yloxy)carbamoyl)-1',5'-dihydrospiro[[1,3]dioxolane-2,4'-pyrrolo[2,3-f]quinoline]-2',9'-dicarboxylate (4)

A mixture of the product from EXAMPLE 2 (3, 95 mg, 0.2 mMol), EDAC.HCl (1-ethyl-3-(3-dimethylaminopropyl)carbodiimide hydrochloride) (104 mg, 0.54 mMol) and HOBT (1-hydroxy-benzotriazole) (73 mg, 0.54 mMol) was placed under a $N_2$ atmosphere. Anhydrous DCM (dichloromethane) (2.5 mL) was added and the resulting mixture was stirred for 2 minutes until a solution was obtained. A solution of 4-penten-1-yl-oxyamine (70 µL, 0.59 mMol) in DCM (1 mL) was added and stirring continued at room temperature for 3 hours. The reaction mixture was diluted with DCM (30 mL), washed with 0.5M HCl (30 mL), and then washed with water (30 mL). The cloudy organic layer was separated and allowed to stand at room temperature for 15 minutes. The organic layer was decanted from some water droplets, dried over $Na_2SO_4$, filtered, and evaporated to a yellow solid. Flash chromatography on silica gel (5 g), eluting with DCM-MeOH (gradient 99.5:5 to 98:2) gave a yellow oil upon evaporation of solvents. Trituration with EtOAc and evaporation of the resulting slurry gave 4 (67 mg, 69%) as a yellow solid after drying in vacuo. MS (AP−) 484 (M−1).

-continued

5

Example 4

4,5-Dioxo-7-((pent-4-en-1-yloxy)carbamoyl)-4,5-dihydro-1H-pyrrolo[2,3-f]quinoline-2,9-dicarboxylic acid (5)

A solution of the product from EXAMPLE 3 (4, 32 mg, 64 µMol) in THF (6 mL) was treated with 1N HCl (0.6 mL) was kept at 45-47° C. for 24 hours. The reaction mixture was cooled to room temperature. TLC (DCM-MeOH 95:5) shows no 4 ($R_f$=0.75) and one major product ($R_f$=0.4). The solution was concentrated on a rotary evaporator to remove THF. The resulting mixture was partitioned between EtOAc (25 mL) and saturated aqueous NaCl (25 mL). The organic layer was separated and allowed to stand for 15 minutes. The organic solution was decanted from some aqueous droplets. It was then evaporated at reduced pressure to give an orange solid. The solid was dissolved in 0.25 M LiOH (1 mL, 0.25 mMol). The resulting black solution was stirred at room temperature for 24 hours. The reaction mixture was then acidified by dropwise addition of concentrated HCl (3 drops from a Pasteur pipet) to give a slurry of an orange solid. The slurry was cooled on an ice bath for 10 minutes then the solid was collected by filtration, rinsing with ice-cold water (2×2 mL) and $Et_2O$ (2×2 mL). The solid was then dried under vacuum for 6 hours to afford 5 (13.5 mg, 51%). MS (AP− taken from a MeOH solution) 444 (M+MeOH−1), 412 (m−1). NMR (DMSO-$d_6$, δ), 13.55 (br, 1H, $CO_2H$), 12.65 (br, 1H, $CO_2H$), 12.02 (br, 1H, CONH), 11.83 (br, 1H, NH), 8.24 (s, 1H, H-8), 7.20 (s, 1H, H-3), 5.87 (m, 1H, vinyl-H), 5.05 (dd, 1H, vinyl-H), 4.99 (dd, 1H, vinyl-H), 4.03 (t, 2H, $OCH_2$), 2.18 (q, 2H, allyl-$CH_2$), 1.75 (m, 2H, $CH_2$).

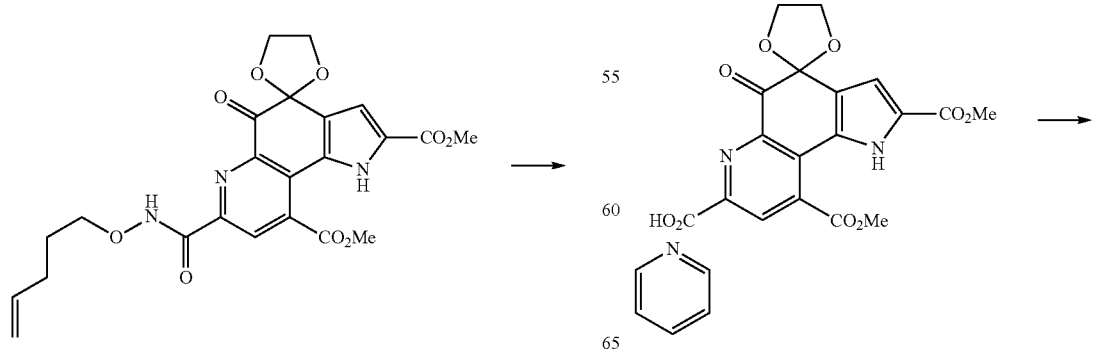

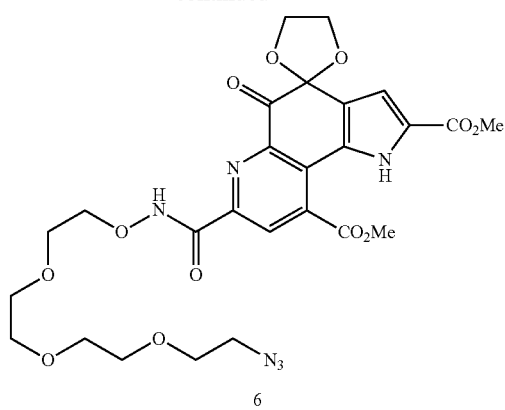

6

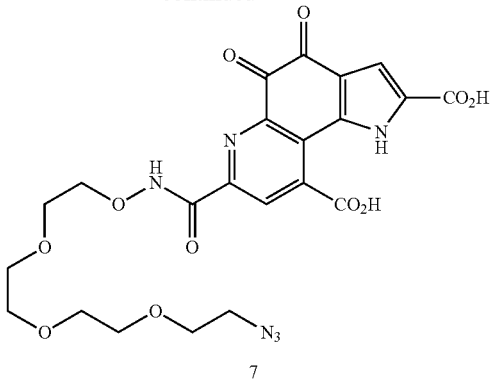

7

Example 6

7-(((11-Azido-3,6,9-trioxaundecyl)oxy)carbamoyl)-4,5-dioxo-4,5-dihydro-1H-pyrrolo[2,3-f]quinoline-2,9-dicarboxylic acid (7)

Example 5

Dimethyl 7'-(((11-azido-3,6,9-trioxaundecyl)oxy)carbamoyl)-5'-oxo-1',5'-dihydrospiro[[1,3]dioxolane-2,4'-pyrrolo[2,3-f]quinoline]-2',9'-dicarboxylate (6)

A mixture of the product from EXAMPLE 2 (3, 390 mg, 0.81 mMol), EDAC.HCl (427 mg, 2.23 mMol) and HOBT (301 mg, 0.2.23 mMol) was placed under a $N_2$ atmosphere. Anhydrous DCM (10 mL) was added and the resulting mixture was stirred for 2 minutes until a solution was obtained. A solution of O-(11-azido-3,6,9-trioxa-undecyl)hydroxylamine (569 mg, 2.43 mMol) in DCM (5 mL) was added and stirring continued at room temperature for 2 hours. The reaction mixture was diluted with DCM (85 mL), washed with 0.5M HCl (100 mL), and then washed with water (100 mL). The cloudy organic layer was separated and allowed to stand at room temperature for 10 minutes. The organic layer was decanted from some water droplets. The previous two steps (standing and decanting) was repeated twice more. Then the solution was dried over $Na_2SO_4$, filtered, and evaporated to a yellow gum. Flash chromatography on silica gel (25 g), eluting with DCM-EtOAc (gradient 97:3 to 85:15), followed by DCM-EtOAc-MeOH (85:13:2) gave a yellow oil upon evaporation of solvents that begins to crystallize on standing. Refrigeration for two days gives a crystalline mass that was pulverized and dried in vacuo to afford 6b (406 mg, 81%). MS (AP– taken from a solution in MeOH) 649 (M+MeOH-1), 617 (m$^{-1}$).

A solution of the product from EXAMPLE 5 (6, 250 mg, 0.4 mMol) in THF (36 mL) was treated with 1N HCl (0.4 mL) was kept at 45-47° C. in for 24 hours. The reaction mixture was cooled to room temperature. TLC (DCM-MeOH 95:5) shows no 4 ($R_f$=0.75) and one major product ($R_f$=0.45). The solution was concentrated on a rotary evaporator to remove THF. The resulting mixture was partitioned between EtOAc (100 mL) and saturated aqueous NaCl (50 mL). The organic layer was separated and allowed to stand for 15 minutes. The organic solution was decanted from some aqueous droplets. The last two steps (standing and decanting) were repeated. The resulting EtOAc solution was then evaporated at reduced pressure to give an orange gum. The gum was dissolved in DCM (20 mL) and evaporated at reduced pressure twice to give an orange foam which was further dried in vacuo for 4 hours. The foam was dissolved in 0.5 M LiOH (3.4 mL, 1.7 mMol). The resulting black solution was stirred at room temperature for 24 hours. The reaction mixture was then acidified by dropwise addition of concentrated HCl (0.25 mL, 3 mMol) to give red solution. The solution was partitioned between EtOAc (50 mL), water (5 mL) and saturated aqueous NaCl (5 mL). The organic layer was separated and allowed to stand for 15 minutes. The organic solution was decanted from some aqueous droplets. Evaporation of solvent at reduced pressure gave a red gum. The gum was triturated with DCM and the resulting slurry was evaporated at reduced pressure. The resulting solid was triturated with DCM-hexanes (1:1), the solvent was decanted from the red-brown solid, and the solid was dried in vacuo to afford 7 (94 mg 43%). MS (AP– taken from a MeOH solution) 577 (M+MeOH-1), 545 (M-1).

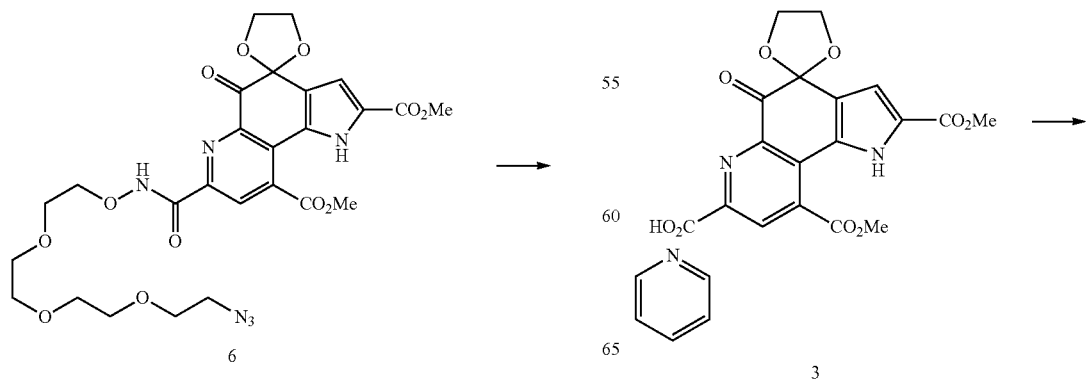

-continued

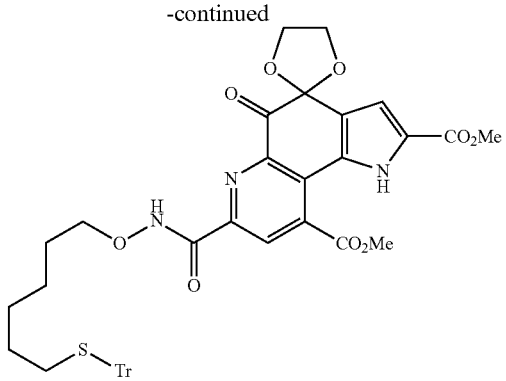

8

Example 7

Dimethyl 5'-oxo-7'-(((6-(tritylthio)hexyl)oxy)carbamoyl)-1',5'-dihydrospiro[[1,3]dioxolane-2,4'-pyrrolo[2,3-f]quinoline]-2',9'-dicarboxylate (8)

A mixture of the product from EXAMPLE 2 (3, 400 mg, 0.83 mMol), EDAC.HCl (440 mg, 2.28 mMol) and HOBT (310 mg, 0.2.28 mMol) was placed under a $N_2$ atmosphere. Anhydrous DCM (10 mL) was added and the resulting mixture was stirred for 2 minutes until a solution was obtained. A solution of O-(6-(tritylthio)hexyl)hydroxylamine (980 mg, 2.49 mMol) in DCM (5 mL) was added and stirring continued at room temperature for 90 minutes. The reaction mixture was diluted with DCM (85 mL), washed with a mixture of water (100 mL) and saturated aqueous $NaHCO_3$ (100 mL). The organic layer was separated and washed with a mixture of 0.2N HCl (100 mL) and saturated aqueous NaCl (50 mL). The organic layer was dried over $Na_2SO_4$, filtered, and evaporated to a yellow oil. Flash chromatography on silica gel (30 g), eluting with DCM-EtOAc (gradient 98:2 to 85:15), followed by DCM-EtOAc-iPrOH (85:13:2) gave a yellow oil upon evaporation of solvents that begins to crystallize on standing. EtOAc (10 mL) was added and the resulting suspension was stirred with a glass rod to pulverize the solid. The solid was collected by filtration, using additional EtOAc (12 mL) to complete the transfer and rinse the solid. Further drying in vacuo at room temperature afforded 8 (420 mg, 65%) as a yellow solid. MS (AP– taken from a solution in MeOH) 806 (M+MeOH-1), 774 ($m^{-1}$). MS (AP+ taken from a solution in MeOH) 806 (M+MeOH+Na), 798 (m+Na).

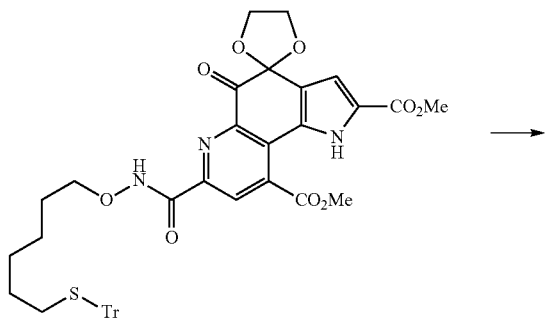

8

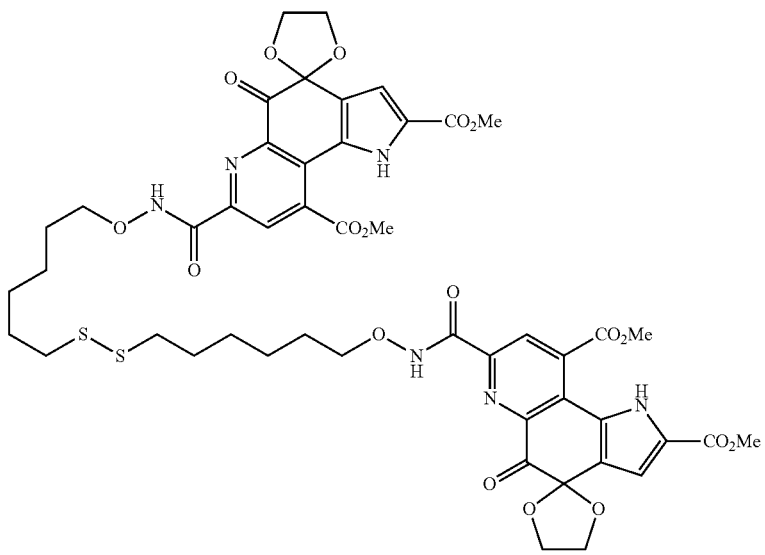

9

Example 8

(Dimethyl 7'-((((6-mercaptohexyl)oxy)carbamoyl)-5'-oxo-1',5'-dihydrospiro[[1,3]dioxolane-2,4'-pyrrolo[2,3-f]quinoline]-2',9'-dicarboxylate)-disulfide (10)

A solution of the product from EXAMPLE 7 (8, 100 mg, 129 µMol) in a mixture of anhydrous DCM (2 mL) and anhydrous MeOH (1 mL) was treated with a solution of $I_2$ in MeOH (15.8 mM, 4.4 mL, 69 µMol). The resulting solution was stirred 40 minutes at room temperature then anhydrous pyridine (21 µL, 260 µMol) was added and stirring was continued for another 40 minutes at room temperature. The reaction mixture was concentrated at reduced pressure. The residue was partitioned between EtOAc (30 mL) and water (30 mL). The organic layer was washed with saturated aqueous NaCl (10 mL), dried over $Na_2SO_4$, filtered, and evaporated at reduced pressure. Flash chromatography on silica gel, eluting with DCM-EtOAc (75:25), followed by DCM-MeOH (97:3) afforded purified 9 (46 mg, 65%). MS (AP− taken from a solution in MeOH) 1128 (M+2MeOH−1), 1096 (m+MeOH−1). MS (AP+ taken from a solution in MeOH) 1151 (M+2MeOH+Na), 1119 (m+MeOH+Na), 1088 (M+Na), 1066 (M+1).

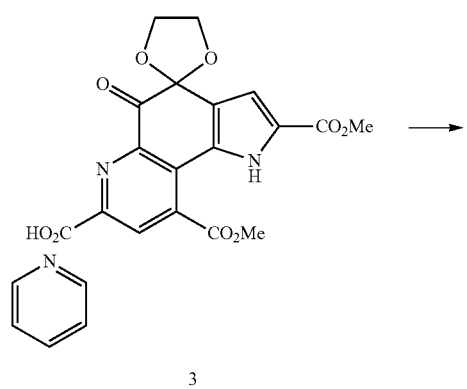

3

Example 9

Dimethyl 7'-(((17,17,18,18,19,19,20,20,21,21,22,22,23,23,24,24,24-heptadecafluoro-14-oxo-3,6,9-trioxa-13-azatetracosyl)oxy)carbamoyl)-5'-oxo-1',5'-dihydrospiro[[1,3]dioxolane-2,4'-pyrrolo[2,3-f]quinoline]-2',9'-dicarboxylate (10)

Using the method of EXAMPLE 5, N-(11-aminooxy-3,6,9-trioxadodecyl)-4,4,5,5,6,6,7,7,8,8,9,9,10,10,11,11,11-heptadecafluoroundecanamide is acylated by 3 to afford 10.

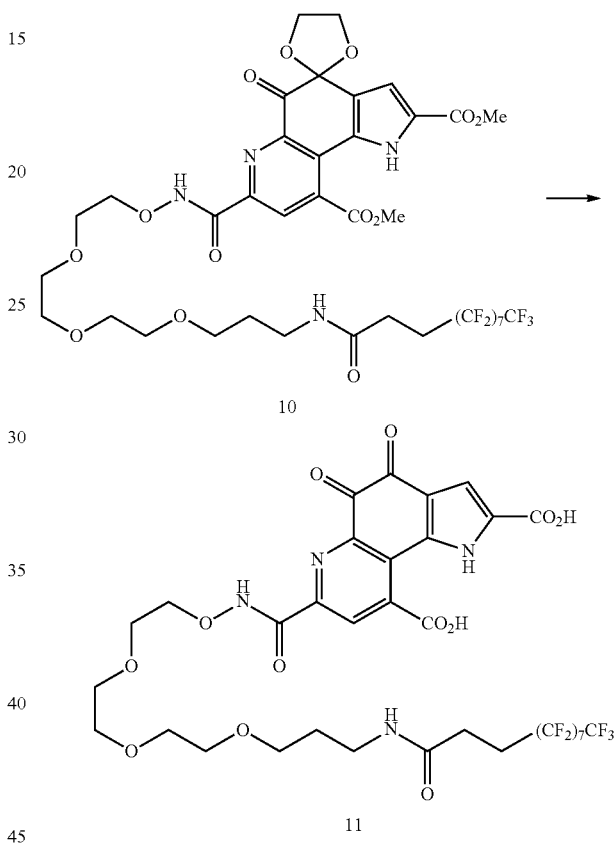

Example 10

7-(((17,17,18,18,19,19,20,20,21,21,22,22,23,23,24,24,24-heptadecafluoro-14-oxo-3,6,9-trioxa-13-azatetracosyl)oxy)carbamoyl)-4,5-dioxo-4,5-dihydro-1H-pyrrolo[2,3-f]quinoline-2,9-dicarboxylic acid (11)

Using the method of EXAMPLE 6, the product from EXAMPLE 9 (compound 10) is deprotected and saponified to afford 11.

Example 11

Conjugation of Compound 7 to Aminoethyl-Agarose Beads

Colorless, low density Aminoethyl-agarose beads (1 mL) may be suspended in MeCN-Pyridine (9:1, 10 mL) and treated with 4-(2,5-dioxo-1-pyrrolidinyl)-2-(diphenylphos-

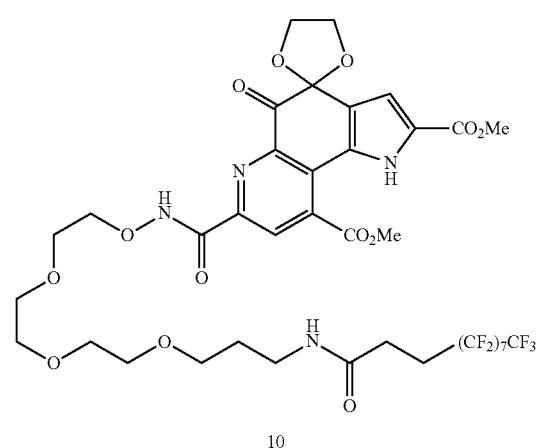

10 phino)-1,4-benzenedicarboxylic acid-1-methyl ester (9, 150 mg). The mixture may then be shaken in a sealed flask for 24 hours. The derivatized beads may then be collected by filtration and washed with MeCN (4×10 mL). The derivatized beads would be ninhydrin negative (no color) as compared to the starting aminoethyl-agarose which would be ninhydrin positive (blue color). The azido-Methoxatin derivative from EXAMPLE 6 (7, 4.0 mg, 7.3 µMol) may be mixed with distilled water (0.4 mL), treated with 0.5 M LiOH (29 µL, 14.5 µMol), and diluted with MeCN (0.6 mL) to afford a red solution. This solution may be added to the derivatized beads. The mixture may then be shaken in a capped vial for 24 hours. The solid may be collected by filtration and rinsed with MeCN—H$_2$O (1:1) until the rinse is colorless. The red color of the solid would indicate the successful conjugation of the azido-Methoxatin (7) to the agarose beads.

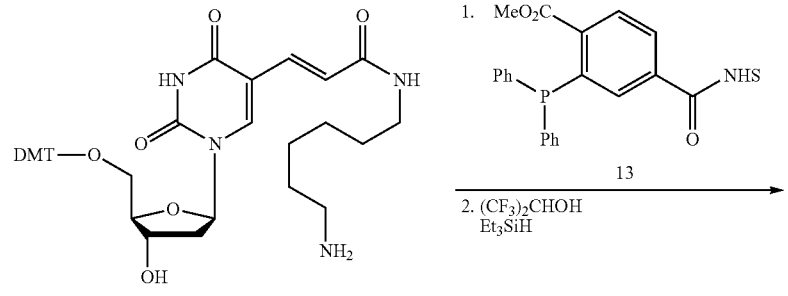

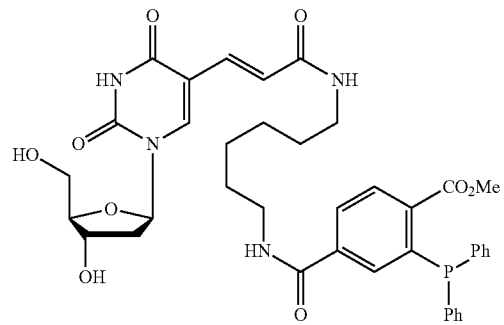

Example 12

Methyl 2-(diphenylphosphino)-4-((6-((E)-3-(1-((2R,4S,5R)-4-hydroxy-5-(hydroxymethyl)tetrahydrofuran-2-yl)-2,4-dioxo-1,2,3,4-tetrahydropyrimidin-5-yl)acrylamido)hexyl)carbamoyl)benzoate (14)

Solid 5-[N-(6-Aminohexyl)-3-(E)-acrylamido]-5'-O-(dimethoxytrityl)-2'-deoxyuridine (12, 0.5 g, 0.72 mMol)) and solid 4-(2,5-dioxo-1-pyrrolidinyl)-2-(diphenylphosphino)-1,4-benzenedicarboxylic acid-1-methyl ester (13, 0.33 g, 0.72 mMol) were placed in a flask under $N_2$ atmosphere. Anhydrous DCM (10 mL) and anhydrous pyridine (1 mL) were added and the mixture was stirred at room temperature for 18 hours. The reaction mixture was partitioned between DCM (25 mL), water (25 mL) and saturated aqueous $NaHCO_3$ (50 mL). The organic layer was separated, dried over $Na_2SO_4$ and filtered. Evaporation of solvent at reduced pressure gave a yellow oil. Flash chromatography on silica gel (25 g), eluting with DCM-MeOH (gradient of 99:1 to 96:4) afforded purified product upon evaporation of solvents at reduced pressure. Further drying in vacuo for 18 hours gave 59 mg of an off-white solid. A portion of this intermediate solid (the DMT protected form of 14, 157 mg, 0.15 mMol) was dissolved a mixture of anhydrous THF (0.5 mL), 1,1,1,3,3,3-hexafluoro-propan-2-ol (1.5 mL) and triethylsilane (0.1 mL, 0.63 mMol) and stirred at room temperature for 24 hours. The reaction mixture was concentrated at reduced pressure to afford a wet paste. Flash chromatography on silica gel (4 g), eluting with DCM-MeOH (a gradient of 100:0 to 90:10) afforded purified product upon evaporation of solvent. Further drying in vacuo at room temperature for 18 hours gave 14 (68 mg, 61%). MS (AP+) 743 (M+1), 765 (M+Na).

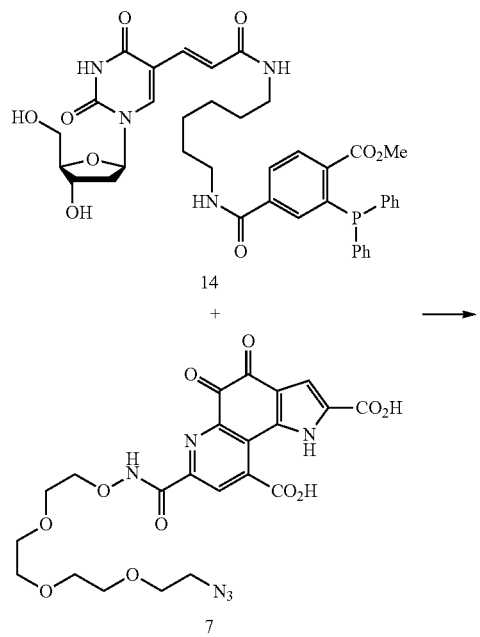

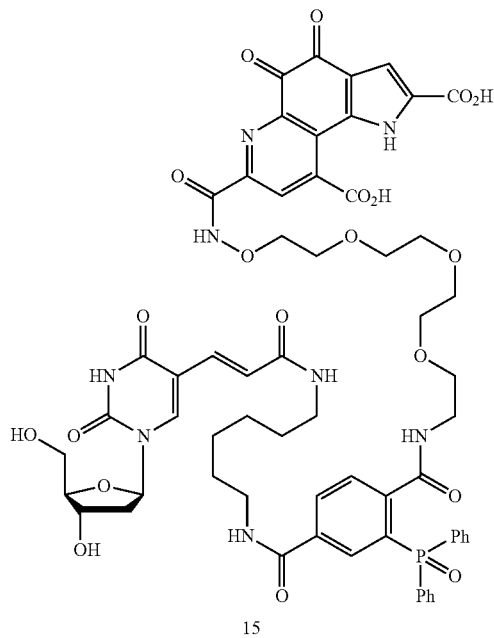

Example 13

7-(((1-(2-(diphenylphosphoryl)-4-((6-((E)-3-(1-((2R,4S,5R)-4-hydroxy-5-(hydroxymethyl)tetrahydrofuran-2-yl)-2,4-dioxo-1,2,3,4-tetrahydropyrimidin-5-yl)acrylamido)hexyl)carbamoyl)phenyl)-1-oxo-5,8,11-trioxa-2-azatridecan-13-yl)oxy)carbamoyl)-4,5-dioxo-4,5-dihydro-1H-pyrrolo[2,3-f]quinoline-2,9-dicarboxylic acid (15)

The product from EXAMPLE 6 (7, 4.0 mg, 7.3 μMol) was mixed with distilled water (0.4 mL) and treated with 0.5 M LiOH (29 μL, 14.5 μMol). The resulting red solution was diluted with MeCN (0.6 mL). The product from EXAMPLE 12 (14, 25 mg, 33.7 nMol) was added in solid form, then the reaction mixture was placed under an atmosphere of $N_2$ and stirred at room temperature for 48 hours. The reaction mixture was diluted with distilled water (0.4 mL) and the resulting solution was concentrated under a stream of $N_2$ gas for approximately 30 minutes until most of the MeCN had evaporated which resulted in a heterogeneous mixture of solid in a red solution. The solid was removed by filtration through a plug of glass wool in a Pasteur pipet, rinsing with distilled water (0.1 mL). The combined filtrate and rinse was extracted with EtOAc (3×0.5 mL). The red aqueous fraction was treated with a stream of $N_2$ gas for approximately 15 minutes, then trace solids were removed by filtration through a plug of glass wool in a Pasteur pipet. The resulting red solution was acidified by addition of 1N HCl (30 μL, 30 nMol) which caused a dark tar to precipitate and stick to the glass. The liquor was withdrawn with a pipet and the tar was rinsed with distilled water (0.5 mL), which was also withdrawn with a pipet. The tar was further dissolved in MeCN—$H_2O$ (1:1, 1 mL) and the solution was evaporated in vacuo at room temperature to afford 15 as a dark orange solid (4 mg, 44%). MS (AP− taken from a MeOH solution) 1278 (M+MeOH-1), 1246 (M−1).

Example 14

Assay of Compounds

The coenzyme activity of several compounds relative to native methoxatin was determined with a published assay that utilizes soluble glucose dehydrogenase (GDH) from *Acinetobactercalcoaceticus*. (Misset-Smits et al., *Methods in Enzymol.*, 280, 89-98 (1997)). Table 1 shows illustrative results for methoxatin and methoxatin derivatives with GDH assay expressed as a percentage of the methoxatin sample. Compounds J and K which modify the 2 position of the methoxatin core displayed less than 0.1% of the activity of the native methoxatin sample. Compounds 5 and 7 displayed 40 and 45%, respectively, of the activity of the native methoxatin sample.

TABLE 1

Relative Activity in GDH Assay

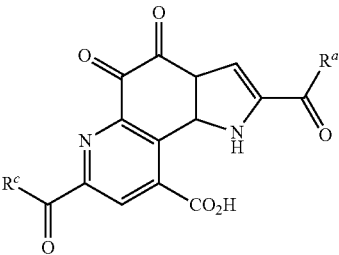

| Compound | $R^c$ | $R^a$ | Relative Activity (%) |
|---|---|---|---|
| Methoxatin | HO | OH | 100 |
| J | HO | O-(n-hexyl) | <0.05 |
| K | HO | $NHO(CH_2)_3CH=CH_2$ | <0.05 |
| 5 | $H_2C=CH(CH_2)_3ONH$ | OH | 45 |
| 7 | $N_3(CH_2CH_2O)_4NH$ | OH | 40 |
| 15 | (Modified Thymidine)-$NH(CH_2CH_2O)_4NH$ | OH | 6 |

What is claimed is:

1. A compound of Formula I, or a salt thereof:

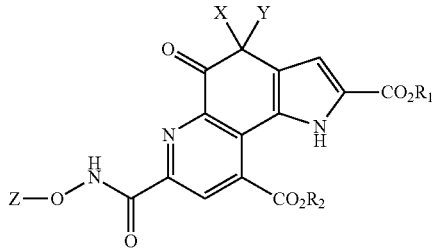

I wherein $R^1$ and $R^2$ are independently selected from the group consisting of H, $-CH_3$, $-C_2H_5$, $-CH_2Ph$, Ph, t-Bu, $-CH_2CH_2Si(CH_3)_3$, $-CH_2CCl_3$, $-CH_2=CHCH_2$, and $-CH_2CH_2CN$;

X and Y are the same and are selected from the group consisting of: $-OH$, $-OCH_3$, $-OC_2H_5$, or $-OCH_2Ph$, or X and Y are taken together to form a cyclic group of $-OCH_2CH_2O-$ or $-OCH_2CH_2CH_2O-$, or X and Y are taken together to form an oxo group (=O);

Z is H, $R^3$-T- or $R^4-S-S-T-$:

T is selected from the group consisting of: $-(CH_2)_n-$, $-(CH_2)_n-(OCH_2CH_2)_m-$, $-(CH_2)_n-(OCH_2CH_2CH_2)_m-$, $-CH_2C(=O)NHO-(CH_2)_n-$, $-CH_2C(=O)NHO-(CH_2)_n-(OCH_2CH_2)_m-$, $-CH_2C(=O)NHO-(CH_2)_n-(OCH_2CH_2CH_2)_m-$, $-(CH_2C(=O)NH)_m-$, $-(CH_2)_n-$, $-(CH_2CH_2C(=O)NH)_m-(CH_2)_n-$, $-(CH_2)_n-(NHC(=O)CH_2)_m-$, $-(CH_2)_n-(OCH_2CH_2)_m-CH_2NHC(O)-$, and $-(NHC(=O)CH_2CH_2)_m-$, wherein n is an integer from 2 to 12, m is an integer from 1 to 6;

$R^3$ is selected from the group consisting of: $H_2C=CH-$,

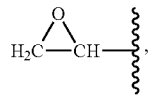

$H_2C=CHCH_2O-$

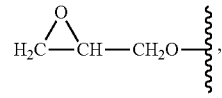

$HOCH_2CH(OH)-$, $HOCH_2CH(OH)CH_2O-$, $HC\equiv C-$, $HC\equiv CCH_2O-$, $(Ph)_3CS-$, $HS-$, $Tr-S-$, $(HO)_2B-$, $(PhO)_2B-$, $(CH_3O)_2B-$, $CF_3(CF_2)_f(CH_2)_g-$, and $-N_3$, wherein f is an integer from 1 to 11, g is 0 or an is an integer from 1 to 3; and $R^4$ is selected from the group consisting of: pyridine-2-yl, 5-nitropyridin-2-yl, $N_3$-T-, $HC\equiv C$-T-, $HC\equiv CCH_2O$-T-, $CF_3(CF_2)_f(CH_2)_g$-T-, $(HO)_2B$-T- and

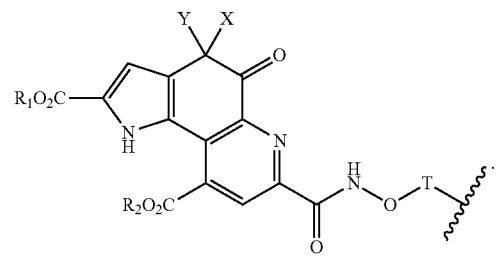

2. The compound of claim 1, wherein $R^1$ and $R^2$ are both H.

3. The compound of claim 2, wherein X and Y are taken together to form an oxo group.

4. The compound of claim 2, wherein X and Y are taken together to form a cyclic group of $-OCH_2CH_2O-$ or $-OCH_2CH_2CH_2O-$.

5. The compound of claim 1, wherein Z is $R^3$-T-.

6. The compound of claim 5, wherein $R^3$ is $HC\equiv CCH_2O-$, $(Ph)_3CS-$, $(HO)_2B-$, $CF_3(CF_2)_f(CH_2)_g-$, or $-N_3$.

7. The compound of claim 6, wherein T is $-(CH_2)_n-$, $-(CH_2)_n-(OCH_2CH_2)_m-$, or $-(CH_2)_n-(OCH_2CH_2CH_2)_m-$.

8. The compound of claim 7, wherein n is from 2 to 6 and m is from 1 to 4.

9. The compound of claim 8, wherein $R^3$ is $CF_3(CF_2)_f(CH_2)_g$—, or —$N_3$.

10. The compound of claim 1, wherein Z is $R^4$—S—S-T-.

11. The compound of claim 10, wherein $R^4$ is $CF_3(CF_2)_f(CH_2)_g$—, pyridine-2-yl, 5-nitropyridin-2-yl, $N_3$-T-, HC≡CCH$_2$O-T-, or

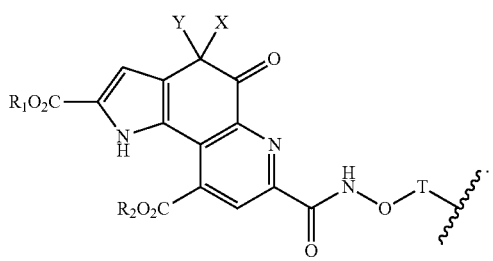

12. The compound of claim 11, wherein T is —$(CH_2)_n$—, —$(CH_2)_n$—$(OCH_2CH_2)_m$—, or —$(CH_2)_n$—$(OCH_2CH_2CH_2)_m$—.

13. The compound of claim 12, wherein n is from 2 to 6 and m is from 1 to 4.

14. The compound of claim 13, wherein $R^4$ is

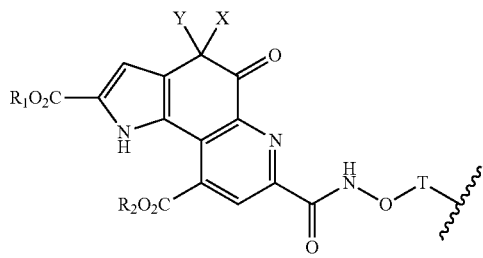

or 5-nitropyridin-2-yl.

15. The compound of claim 1, wherein said compound is selected from the group consisting of:

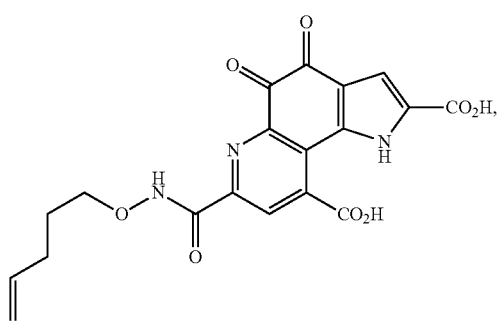

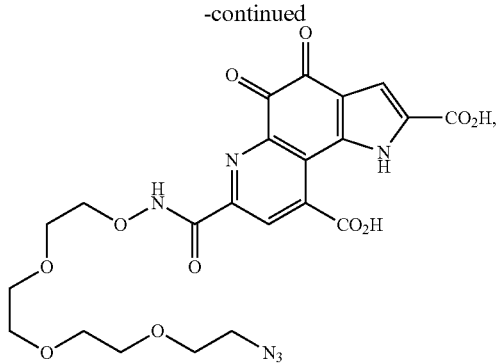

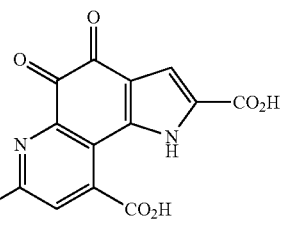

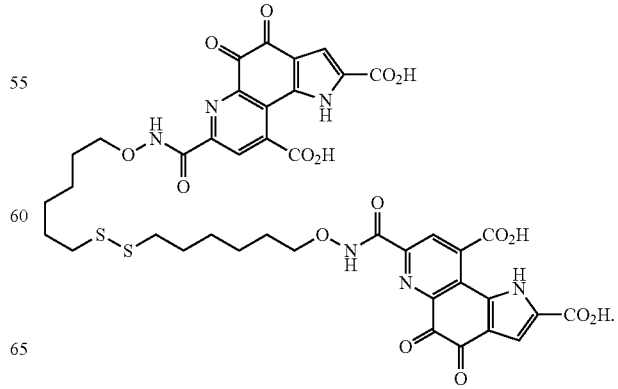

16. The compound of claim 1, wherein said compound is selected from the group consisting of:
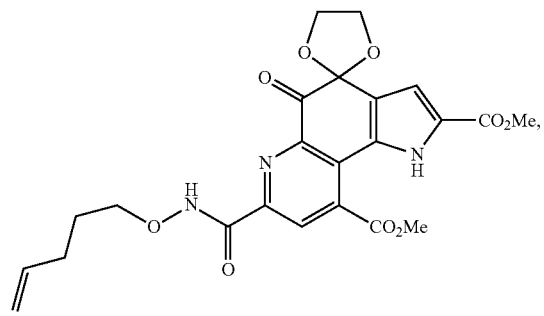
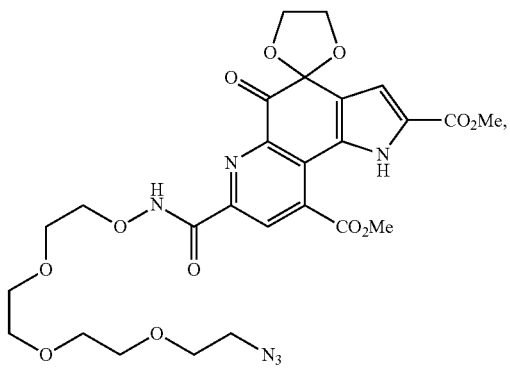
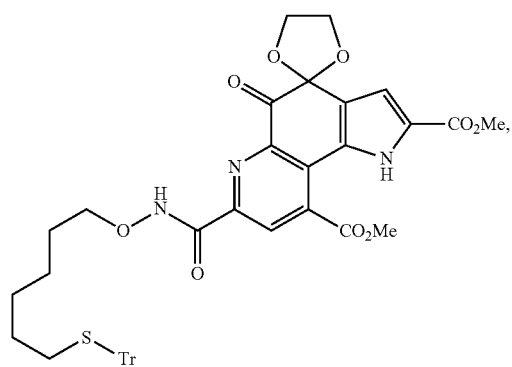
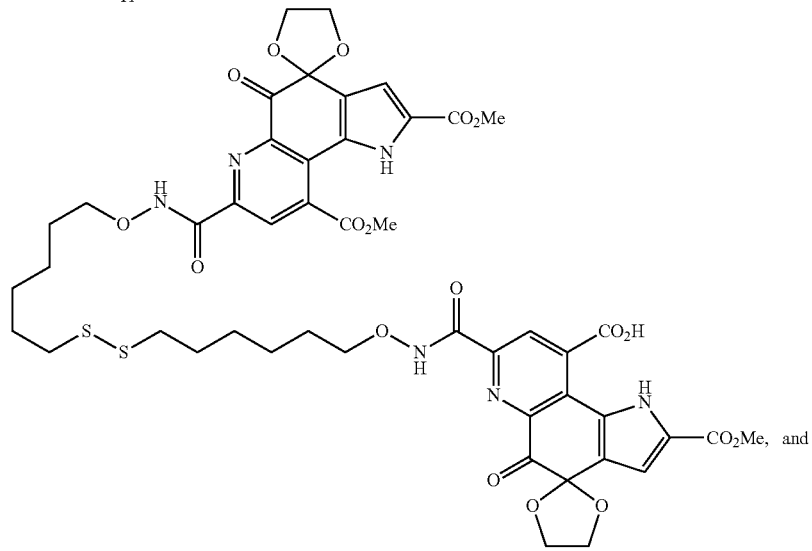
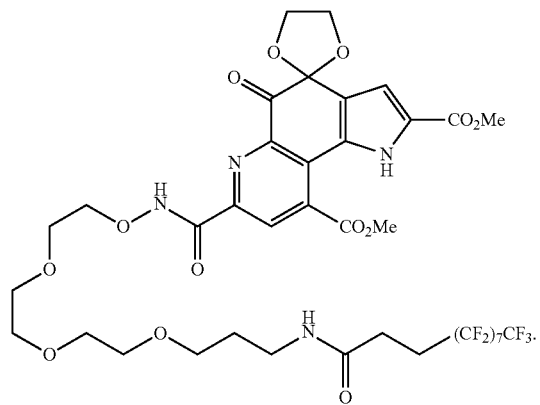

17. A compound of formula II, or a base addition salt thereof:

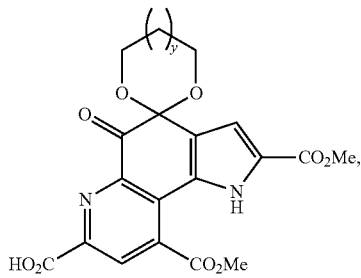

wherein y is 0 or 1.

18. The compound of claim 17, wherein said compound is

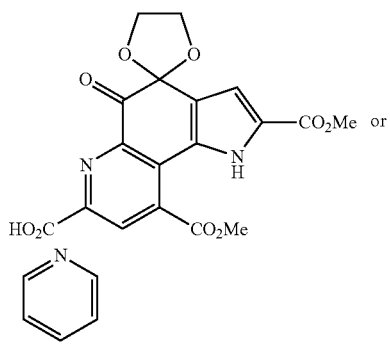

or

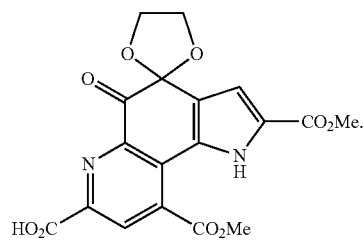

19. A method of synthesizing a compound of formula II, or a pyridine salt thereof:

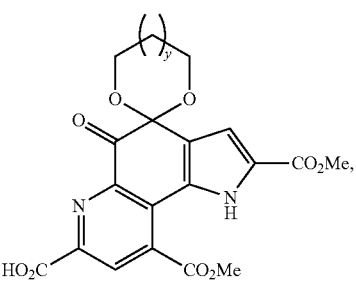

comprising contacting a compound of formula V

III

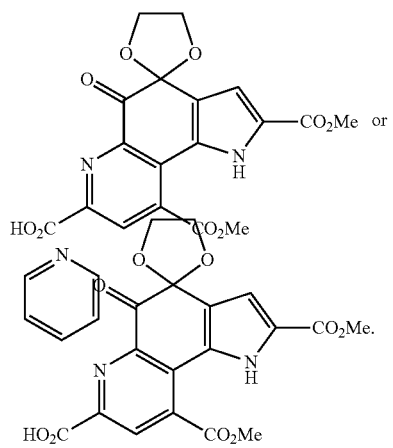

wherein y is 0 or 1, with a mixture of about 1 to about 5 parts pyridine to one part water for at least about 2 days at 20 to 30° C.

20. The method of claim 19, wherein said compound of formula II is:

* * * * *

UNITED STATES PATENT AND TRADEMARK OFFICE
CERTIFICATE OF CORRECTION

PATENT NO. : 8,198,290 B2
APPLICATION NO. : 12/646234
DATED : June 12, 2012
INVENTOR(S) : John C. Hodges Page 1 of 2

It is certified that error appears in the above-identified patent and that said Letters Patent is hereby corrected as shown below:

In the Specification

In column 7, line 59, before "10% activity of native" insert --greater than--.

In the Claims

In column 27, claim 16, third formula, replace entire formula with the following formula:

-- 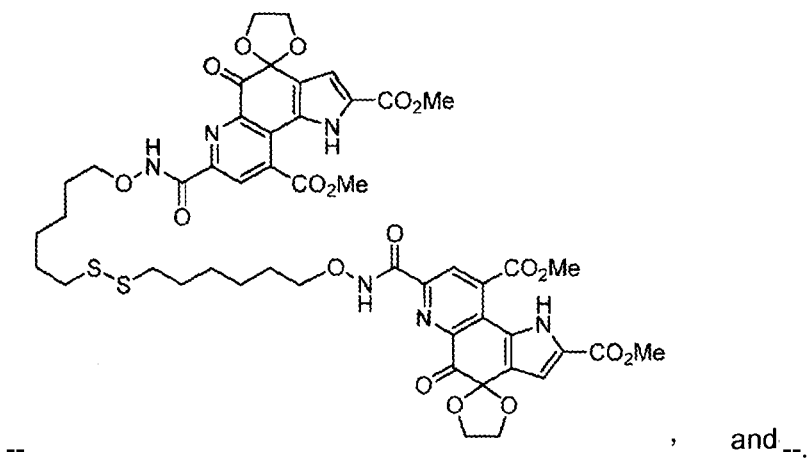 , and --.

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 8,198,290 B2

In the Claims (cont'd)

In column 30, claim 20, replace the formulas with the following formulas:

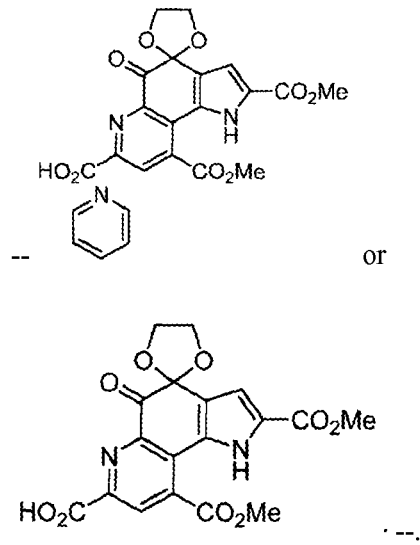

-- or --.